(12) United States Patent
Mechael et al.

(10) Patent No.: US 9,864,792 B1
(45) Date of Patent: *Jan. 9, 2018

(54) SYSTEMS AND METHODS FOR DATA MIGRATION

(71) Applicant: ALLSCRIPTS SOFTWARE, LLC, Chicago, IL (US)

(72) Inventors: George Rizk Mechael, Waltham, MA (US); Laurie A. Hart, Carver, MA (US); Angela Hodgetts, Atlanta, GA (US); Pamela Fleury, Brookline, NH (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/462,830

(22) Filed: Mar. 18, 2017

Related U.S. Application Data (63) Continuation of application No. 14/144,873, filed on Dec. 31, 2013, now Pat. No. 9,607,066.

(60) Provisional application No. 61/868,506, filed on Aug. 21, 2013.

(51) Int. Cl.
*G06F 17/30* (2006.01)
*G06F 3/0482* (2013.01)
*G06F 19/00* (2011.01)
*G06F 3/0488* (2013.01)

(52) U.S. Cl.
CPC ...... *G06F 17/30575* (2013.01); *G06F 3/0482* (2013.01); *G06F 17/303* (2013.01); *G06F 17/30557* (2013.01); *G06F 19/322* (2013.01); *G06F 19/3406* (2013.01); *G06F 3/0488* (2013.01)

(58) Field of Classification Search
CPC .................................................... G06F 17/303
USPC ......................................................... 707/610
See application file for complete search history.

(56) References Cited

U.S. PATENT DOCUMENTS

| | | | |
|---|---|---|---|
| 2003/0023580 A1* | 1/2003 | Braud | G06Q 50/22 |
| 2003/0069758 A1* | 4/2003 | Anderson | G06F 19/322 705/3 |
| 2003/0200226 A1* | 10/2003 | Wells | G06F 17/30893 |
| 2006/0106877 A1* | 5/2006 | Lee | G06F 17/3028 |
| 2006/0235899 A1* | 10/2006 | Tucker | G06F 17/303 |
| 2008/0244148 A1* | 10/2008 | Nix, Jr. | H04L 41/0856 710/313 |

(Continued)

OTHER PUBLICATIONS

Manual entitled "Clicktate User Manual", dated Aug. 2012, by Clicktate.*

*Primary Examiner* — Mahesh Dwivedi
(74) *Attorney, Agent, or Firm* — Tillman Wright, PLLC; Chad D. Tillman; Jeremy C. Doerre (57) ABSTRACT

A method includes importing legacy data from a legacy application into a new system by storing the legacy data in a database separate from data native to the new system; displaying, to a user via a display screen, an interface configured to allow a user to view both legacy data and data native to the new system; displaying, to the user via a display screen, an interface including information of the legacy data that is associated with a particular patient account, one or more interface elements configured to allow the user to perform limited actions with respect to the particular patient account associated with the information, and a user interface element configured to allow a user to selectively activate the patient account.

10 Claims, 9 Drawing Sheets

(56) References Cited

U.S. PATENT DOCUMENTS

| | | | |
|---|---|---|---|
| 2008/0306986 A1* | 12/2008 | Doyle, Sr. | G06Q 10/10 |
| 2011/0087683 A1* | 4/2011 | Paparella | G06F 17/30563 707/756 |
| 2011/0301982 A1* | 12/2011 | Green, Jr. | G06F 19/3443 705/3 |
| 2012/0166219 A1* | 6/2012 | Mansour | G06F 19/321 705/3 |
| 2014/0195514 A1* | 7/2014 | Stein | G06F 17/30566 707/722 |

* cited by examiner

SYSTEMS AND METHODS FOR DATA MIGRATION

CROSS-REFERENCE TO RELATED APPLICATION

The present application is a U.S. continuation patent application of, and claims priority under 35 U.S.C. §120 to, U.S. nonprovisional patent application Ser. No. 14/144,873, filed Dec. 31, 2013, now U.S. Pat. No. 9,607,066, which '873 application and '066 patent are incorporated by reference herein, and which '873 application is a U.S. nonprovisional patent application of, and claims priority under 35 U.S.C. §119(e) to, U.S. provisional patent application 61/868,506, filed Aug. 21, 2013, which '506 provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to data migration.

When an entity is moving from an old system to a new system there is a need to migrate or move existing data from the old system into the new system.

Needs exist for improvement in data migration. These, and other needs, are addressed by one or more aspects of the present invention.

SUMMARY OF THE INVENTION

The present invention includes many aspects and features. Moreover, while many aspects and features relate to, and are described in, the context of healthcare records, the present invention is not limited to use only in healthcare records, as will become apparent from the following summaries and detailed descriptions of aspects, features, and one or more embodiments of the present invention.

Accordingly, one aspect of the present invention relates to a method comprising importing legacy data from a legacy application into a new system by storing the legacy data in a database separate from data native to the new system; displaying, to a user via a display screen, an interface configured to allow a user to view both legacy data and data native to the new system; displaying, to the user via a display screen, an interface including information of the legacy data that is associated with a particular patient account, one or more interface elements configured to allow the user to perform limited actions with respect to the particular patient account associated with the information, and a user interface element configured to allow a user to selectively activate the patient account; receiving, from the user via one or more input devices, input corresponding to engagement of the user interface element configured to allow a user to selectively activate the patient account; in response to receiving input corresponding to engagement of the user interface element configured to allow a user to selectively activate the patient account, migrating the information of the legacy data that is associated with the particular patient account to a native database of the new system.

In a feature of this aspect, the electronic device comprises a laptop.

In a feature of this aspect, the electronic device comprises a tablet.

In a feature of this aspect, the electronic device comprises a phone.

In a feature of this aspect, the electronic device comprises a computer.

In a feature of this aspect, the one or more input devices comprise a touch screen.

In a feature of this aspect, the one or more input devices comprise a mouse.

In a feature of this aspect, the one or more input devices comprise a keyboard.

In a feature of this aspect, the legacy application comprises an application configured for use in a health care context.

In a feature of this aspect, the new system comprises a system configured for use in a health care context.

Another aspect relates to a method comprising importing legacy data from a legacy application into a new system by storing the legacy data in a mirror database separate from data native to the new system; displaying, to a user via a display screen, an interface configured to allow a user to view both legacy data and data native to the new system; displaying, to the user via a display screen, an interface including information of the legacy data that is associated with a particular patient account, one or more interface elements configured to allow the user to perform limited actions with respect to the particular patient account associated with the information, and a user interface element configured to allow a user to selectively activate the patient account; receiving, from the user via one or more input devices, input corresponding to engagement of one of the user interface elements configured to allow the user to perform limited actions with respect to the particular patient account associated with the information, the one of the user interface elements being a user interface element configured to post a payment against a visit; in response to receiving input corresponding to engagement of one of the user interface elements configured to allow the user to perform limited actions with respect to the particular patient account associated with the information, automatically reducing a balance in both the mirror database and a native database that stores data native to the new system.

Another aspect relates to one or more computer readable media containing computer executable instructions for performing a methodology in accordance with one or more preferred implementations.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As noted hereinabove, when an entity is moving from an old system to a new system, there is a need to migrate or move existing data from the old system into the new system. For example, a healthcare entity migrating from an old financial manager application to new financial manager application might need to move data incorporating historical accounts and active accounts, as well as associated financial data.

In one or preferred implementations, data is imported from a first source (such as a legacy source) into an application configured to store data in a different structure or format. In one or more preferred implementations, such data is imported to mirror such application structure or format, but is housed separately, e.g. in a legacy database.

In one or more preferred implementations, such data can be accessed via the application with limited functionality, for example only "view" functionality might be provide. In one or more preferred implementations, data in both a "live" database and a "mirrored" database can be updated based on transactions. For example, in a preferred methodology, posting a payment against a visit might reduce a balance in both a mirrored database and a live database.

Preferably, records that are stored in a mirrored database can be selectively activated when needed. In one or more preferred implementations, selective activation, rather than a full import, is believed to possibly minimize use of system resources and increase performance.

In one or more preferred implementations, an application provides users the ability to migrate selected legacy data into a new, target system and provides some, limited functionality for the legacy data. In an exemplary preferred implementation for a financial application for healthcare entities, users will have the ability to view migrated data, post payments and adjustments, and generate reports as needed. Preferably, the migrated data is housed within the target system but remains independent from data native to the target system. Preferably, the migrated data is segmented into different tables within the target system until activated. This lowers the risk of contamination or corruption to the target system's native accounts, while allowing users the ability to reconcile, maintain, or close all active and historical accounts.

In one or more preferred implementations, a user is able to activate individual accounts for full functionality based on business need. In one or more preferred implementations, a user has the ability to perform functions within an application such as billing, rebilling, charge entry or reversal, claim release, patient guarantor billing, generation of statements, etc.

Figure 1:
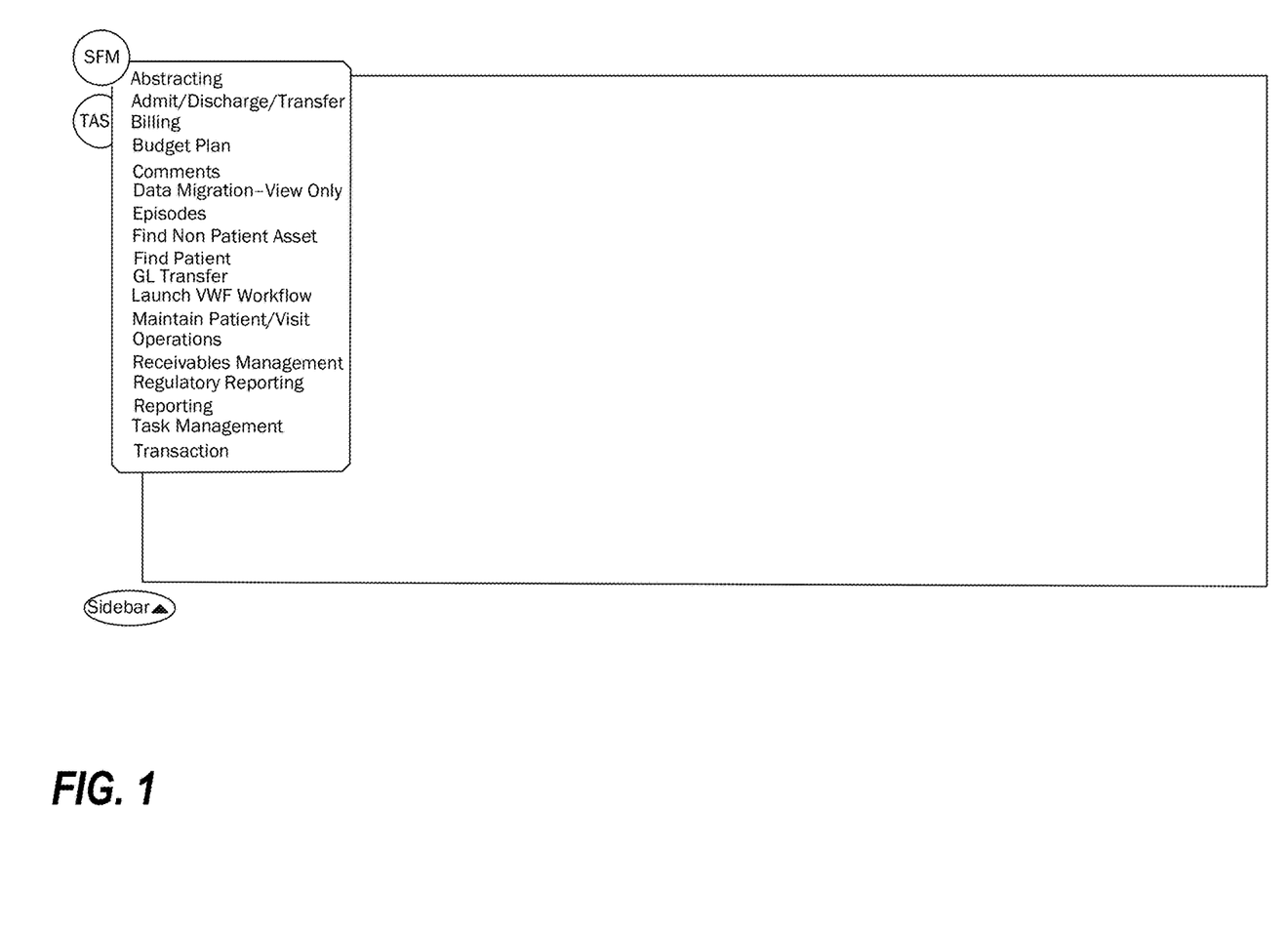
FIG. 1 illustrates an exemplary menu interface for an application.

FIG. 1 illustrates an exemplary menu interface for an application. As illustrated, the menu interface includes an option to view migrated data.

Figure 2:
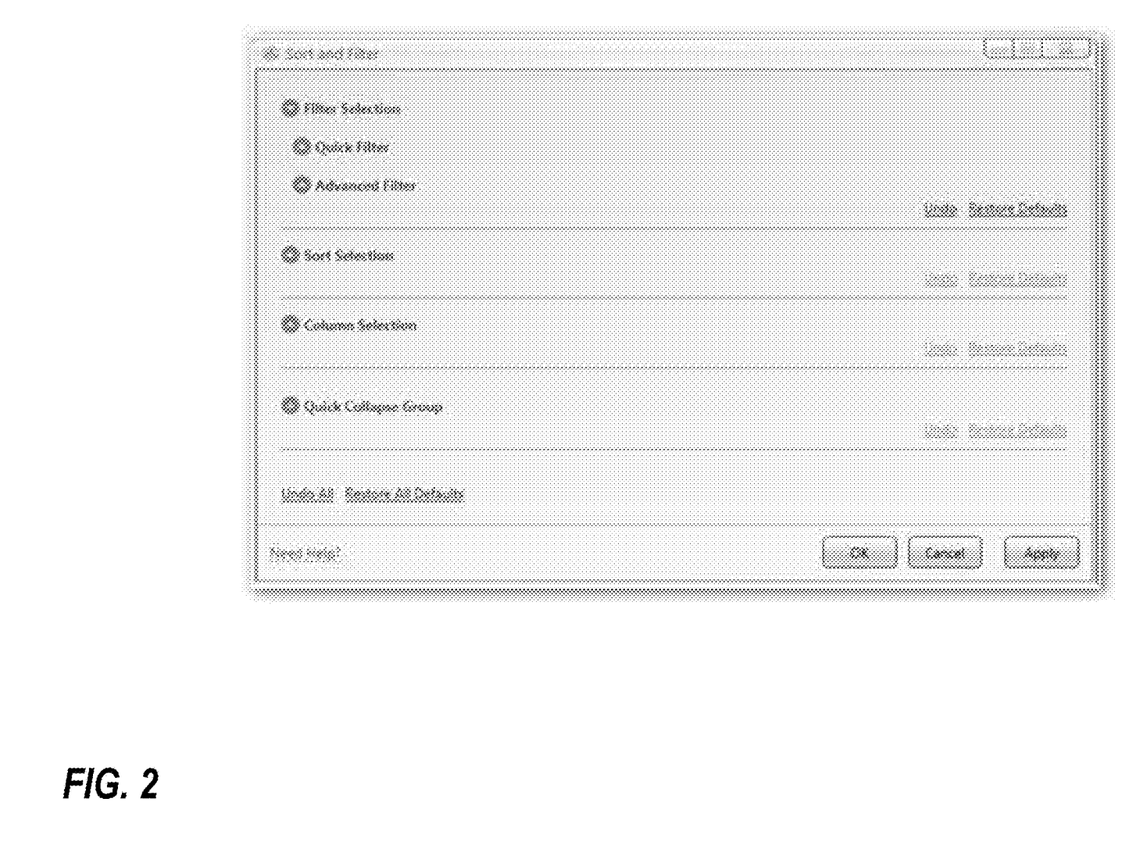
FIG. 2 illustrates an exemplary sort and filter interface in accordance with one or more preferred implementations.

In one or more preferred implementations, a user can sort and filter data, e.g. to drill down to specific patients to view data for. FIG. 2 illustrates an exemplary sort and filter interface in accordance with one or more preferred implementations.

Figure 3:
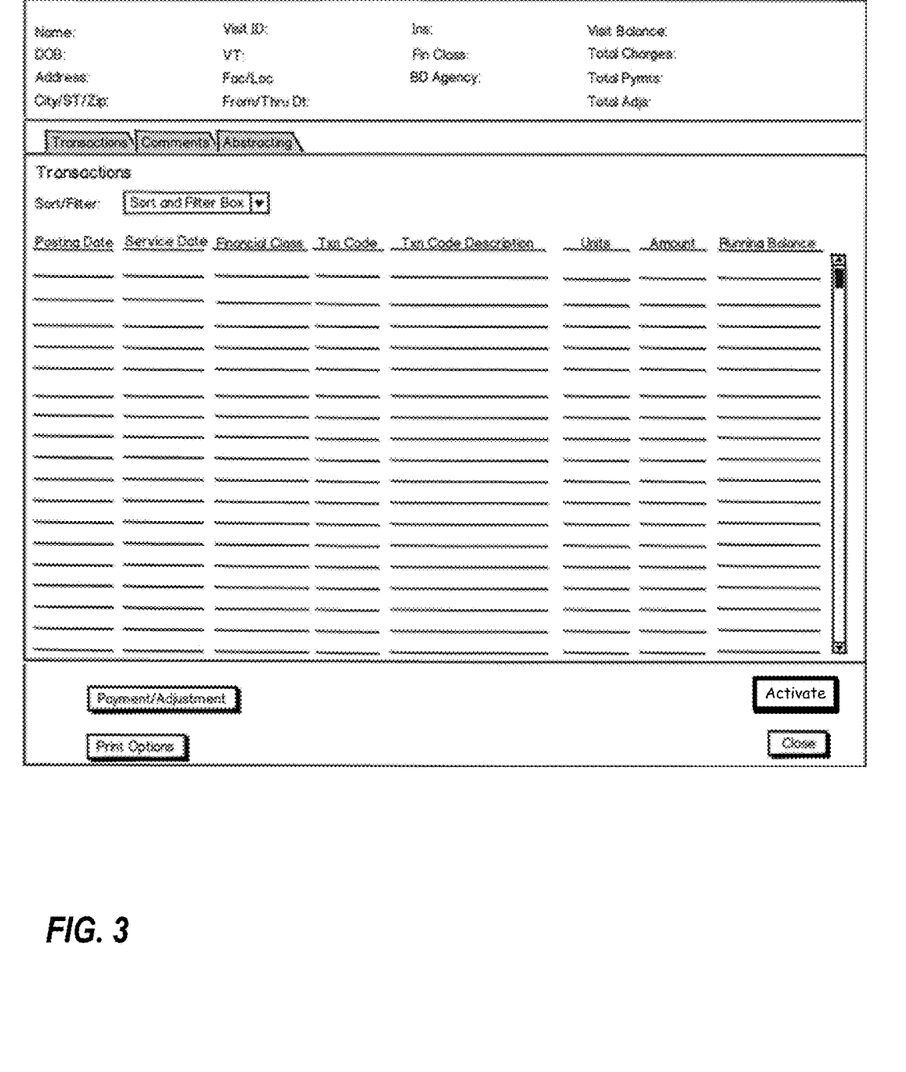
FIG. 3 illustrates an exemplary visit transactions interface which displays detailed visit information for a selected patient.

FIG. 3 illustrates an exemplary visit transactions interface which displays detailed visit information for a selected patient. In one or more preferred implementations, the interface includes a button configured to activate the account for full functionality.

Figure 4:
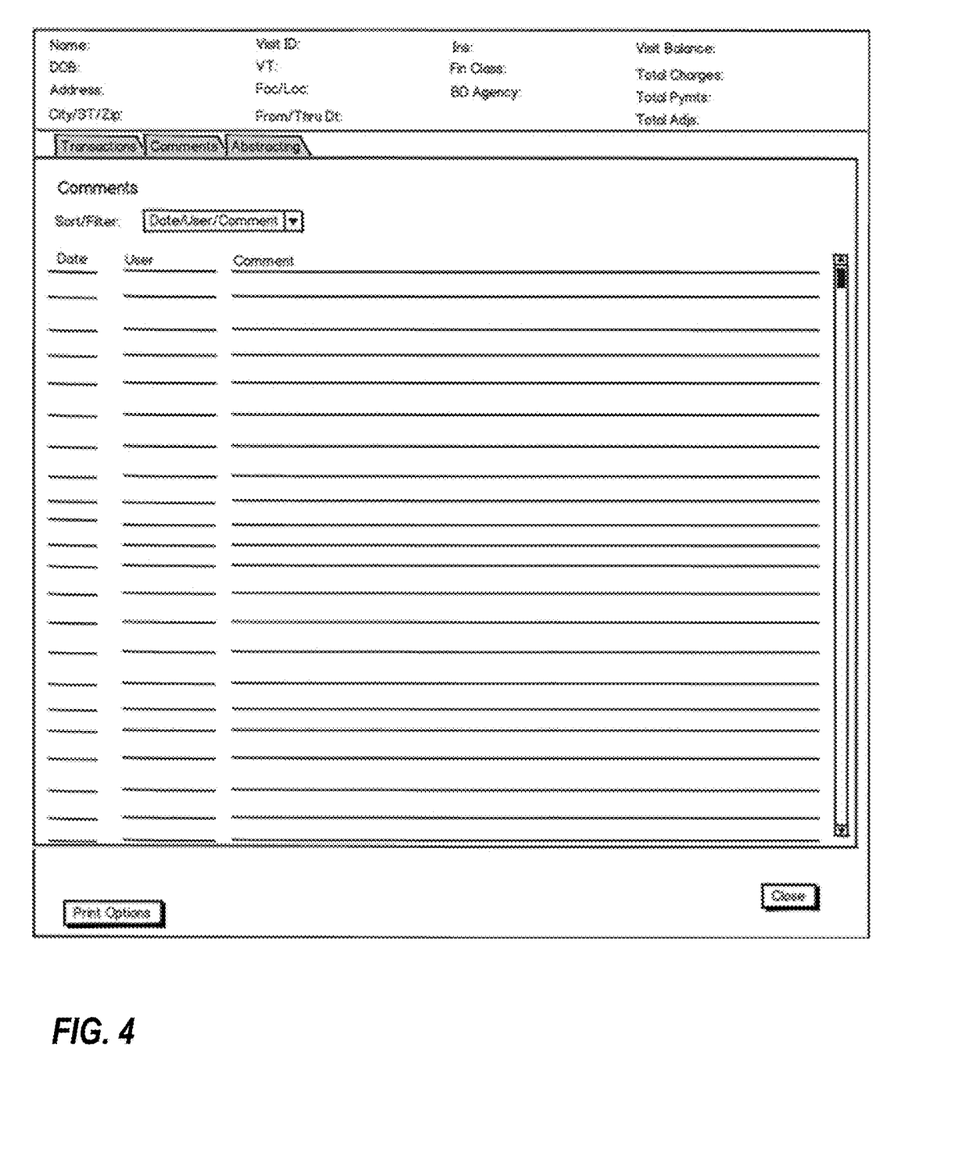
FIG. 4 illustrates an exemplary comments interface which displays comments that were migrated related to the visit in context.

FIG. 4 illustrates an exemplary comments interface which displays comments that were migrated related to the visit in context.

Figure 5:
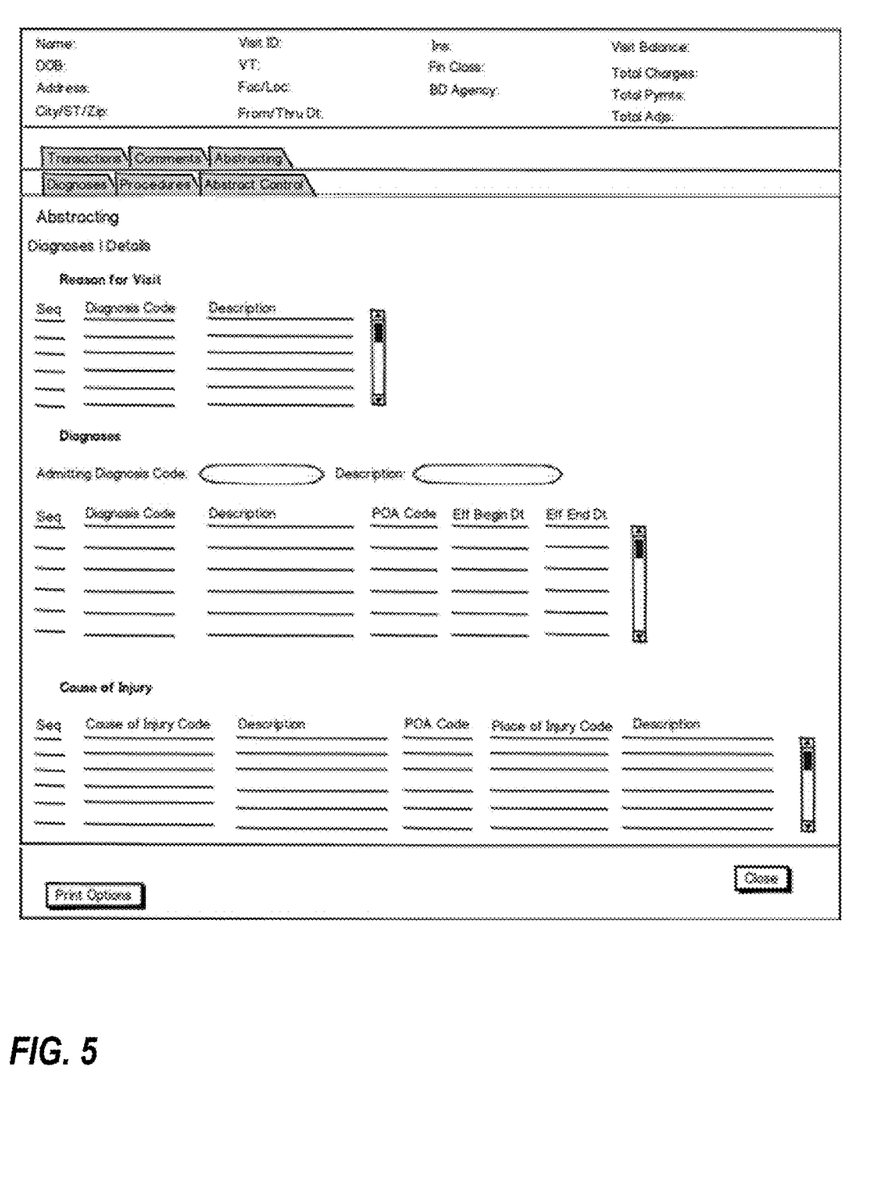
FIG. 5 illustrates an exemplary diagnoses visit abstracting interface which displays abstracted diagnosis information related to the visit in context.

FIG. 5 illustrates an exemplary diagnoses visit abstracting interface which displays abstracted diagnosis information related to the visit in context.

Figure 6:
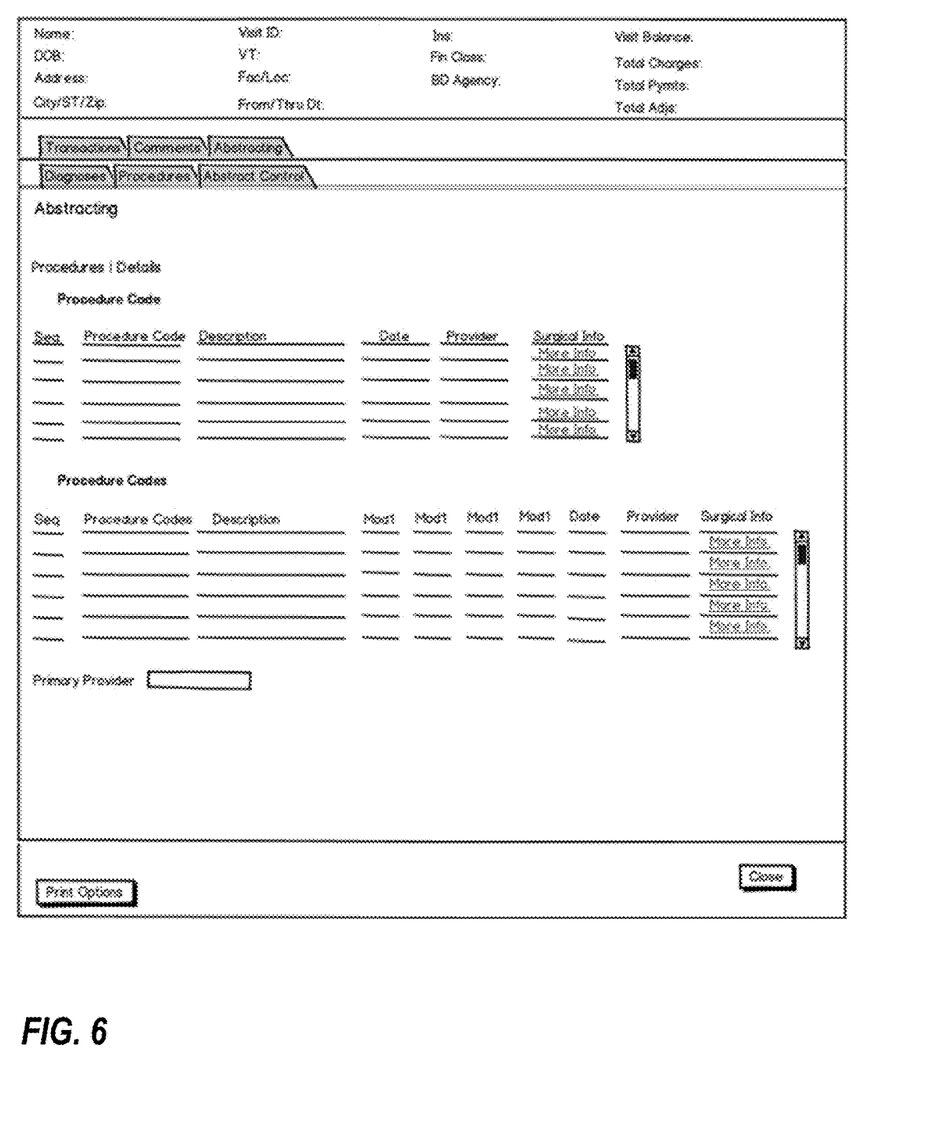
FIG. 6 illustrates an exemplary procedures visit abstracting interface which displays abstracted procedure information related to the visit in context.

FIG. 6 illustrates an exemplary procedures visit abstracting interface which displays abstracted procedure information related to the visit in context.

Figure 7:
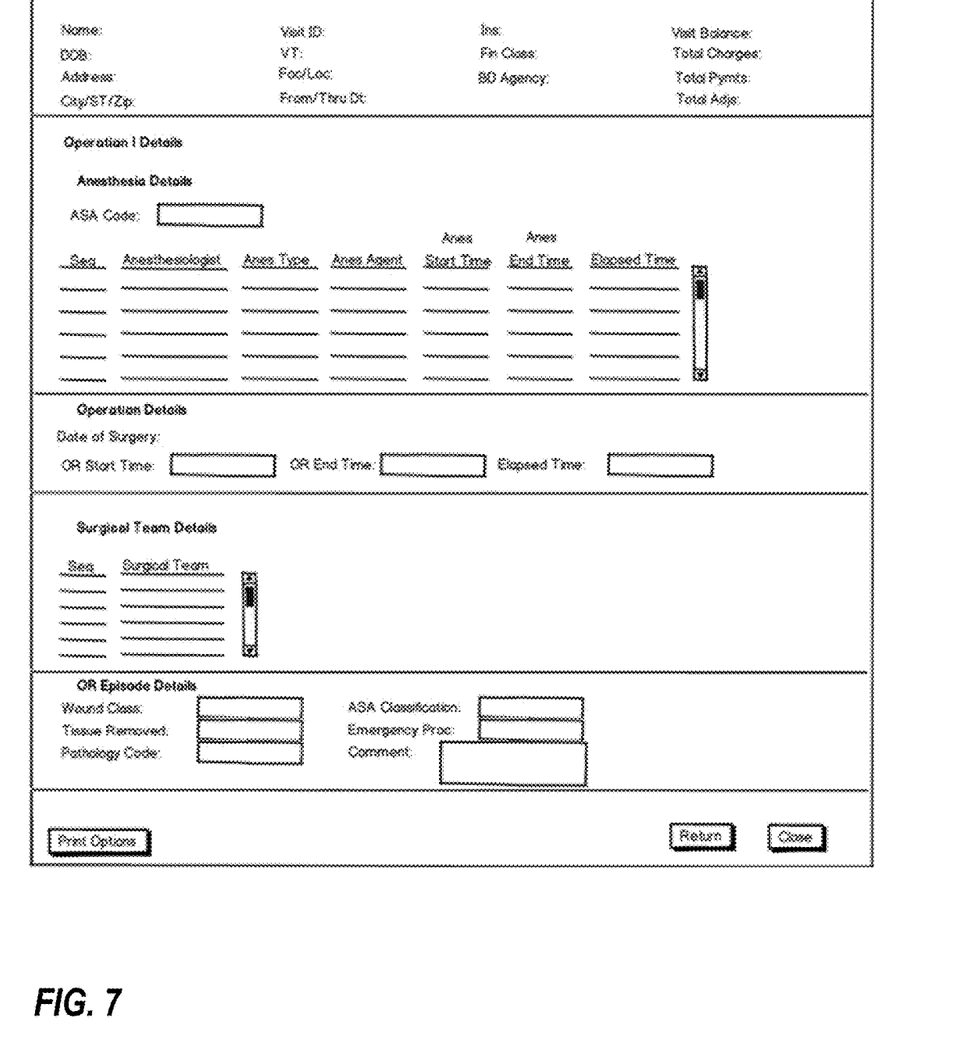
FIG. 7 illustrates an exemplary surgical info procedures visit abstracting interface which displays abstracted surgical information related to the visit in context.

FIG. 7 illustrates an exemplary surgical info procedures visit abstracting interface which displays abstracted surgical information related to the visit in context.

Figure 8:
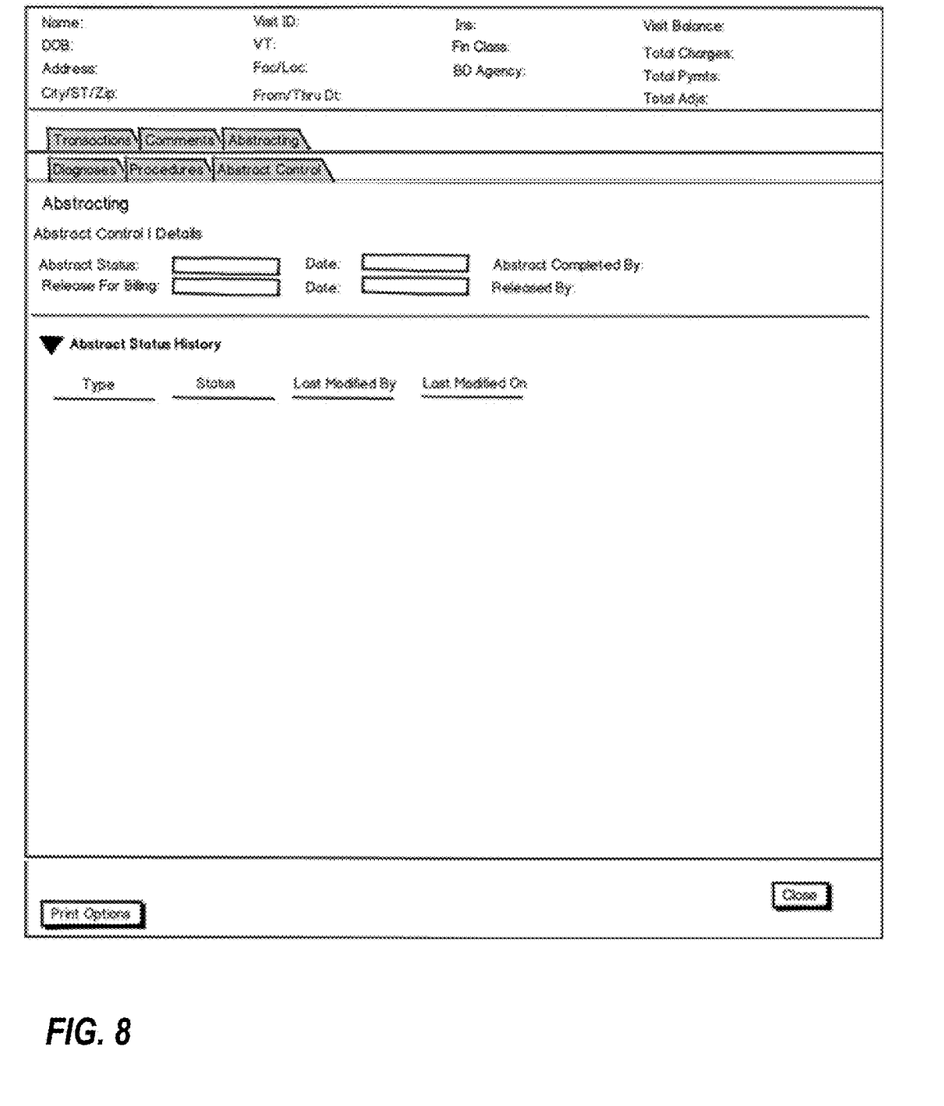
FIG. 8 illustrates an exemplary abstracting control interface which displays the abstracting status of migrated data.

FIG. 8 illustrates an exemplary abstracting control interface which displays the abstracting status of migrated data.

Figure 9:
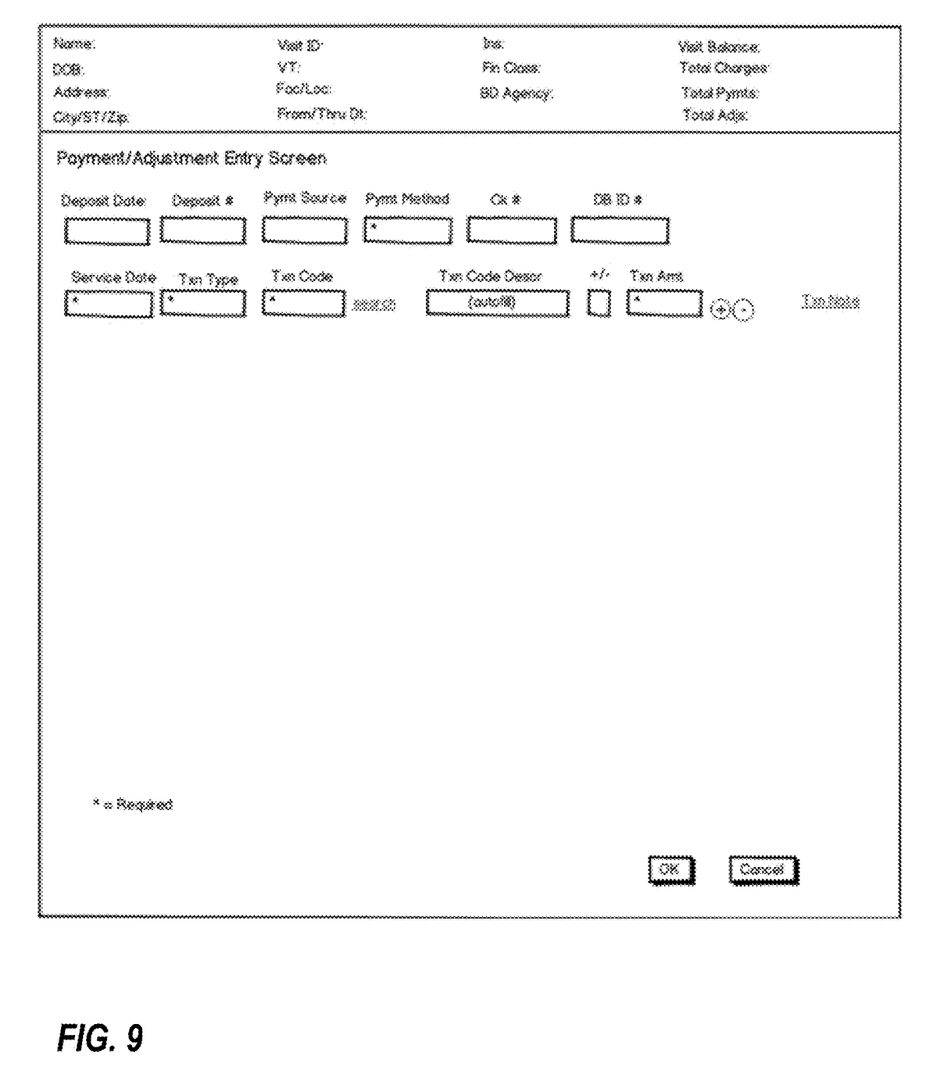
FIG. 9 illustrates an exemplary payment/adjustment interface which allows a user to post payments and adjustments to migrated data.

FIG. 9 illustrates an exemplary payment/adjustment interface which allows a user to post payments and adjustments to migrated data.

In one or more preferred implementations, a report writer is configured to allow a user to custom design and generate reports as needed from migrated data.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
   (a) importing legacy data from a legacy application into a new system by storing the legacy data in a legacy database separate from data native to the new system;
   (b) maintaining, at the new system,
      (i) a first balance for a particular patient account in the legacy database, and
      (ii) a second balance for the particular patient account in a native database that stores data native to the new system,
      (iii) wherein the first balance in the legacy database and the second balance in the native database are maintained to remain independent of one another;
   (c) displaying, to a user via a display screen, an interface configured to allow a user to view both legacy data and data native to the new system;
   (d) displaying, to the user via a display screen, an interface including
      (i) information of the legacy data that is associated with the particular patient account,
      (ii) one or more interface elements configured to allow the user to perform limited actions with respect to the particular patient account associated with the information, and
      (iii) a user interface element configured to allow a user to selectively activate the particular patient account;
   (e) receiving, from the user via one or more input devices, input corresponding to engagement of one of the user interface elements configured to allow the user to perform limited actions with respect to the particular patient account associated with the information; and
   (f) in response to receiving input corresponding to engagement of one of the user interface elements configured to allow the user to perform limited actions with respect to the particular patient account associated with the information, automatically updating both the first balance in the legacy database and the second balance in the native database while maintaining the independence of such balances by
      (i) reducing the first balance in the legacy database causing the first balance to have a first value, and
      (ii) reducing the second balance in the native database that stores data native to the new system causing the second balance to have a second value different than the first value.

2. The method of claim 1, wherein the one or more input devices comprises a laptop.

3. The method of claim 1, wherein the one or more input devices comprises a tablet.

4. The method of claim 1, wherein the one or more input devices comprises a phone.

5. The method of claim 1, wherein the one or more input devices comprises a computer.

6. The method of claim 1, wherein the one or more input devices comprise a touch screen.

7. The method of claim 1, wherein the one or more input devices comprise a mouse.

8. The method of claim 1, wherein the one or more input devices comprise a keyboard.

9. The method of claim 1, wherein the legacy application comprises an application configured for use in a health care context.

10. One or more non-transitory computer readable media containing computer executable instructions configured to perform a method comprising:
  (a) importing legacy data from a legacy application into a new system by storing the legacy data in a legacy database separate from data native to the new system;
  (b) maintaining, at the new system,
    (i) a first balance for a particular patient account in the legacy database, and
    (ii) a second balance for the particular patient account in a native database that stores data native to the new system,
    (iii) wherein the first balance in the legacy database and the second balance in the native database are maintained to remain independent of one another;
  (c) displaying, to a user via a display screen, an interface configured to allow a user to view both legacy data and data native to the new system;
  (d) displaying, to the user via a display screen, an interface including
    (i) information of the legacy data that is associated with the particular patient account,
    (ii) one or more interface elements configured to allow the user to perform limited actions with respect to the particular patient account associated with the information, and
    (iii) a user interface element configured to allow a user to selectively activate the particular patient account;
  (e) receiving, from the user via one or more input devices, input corresponding to engagement of one of the user interface elements configured to allow the user to perform limited actions with respect to the particular patient account associated with the information; and
  (f) in response to receiving input corresponding to engagement of one of the user interface elements configured to allow the user to perform limited actions with respect to the particular patient account associated with the information, automatically updating both the first balance in the legacy database and the second balance in the native database while maintaining the independence of such balances by
    (i) reducing the first balance in the legacy database causing the first balance to have a first value, and
    (ii) reducing the second balance in the native database that stores data native to the new system causing the second balance to have a second value different than the first value.

* * * * *